US006415045B1

(12) United States Patent
Quigley et al.

(10) Patent No.: US 6,415,045 B1
(45) Date of Patent: Jul. 2, 2002

(54) PAPERMAKING FABRIC ANALYSIS REPORT

(75) Inventors: Scott D. Quigley, Townville; Sue Henderson, Greenville, both of SC (US)

(73) Assignee: Wagner Systems Corporation, Greenville, SC (US)

( * ) Notice: Subject to any disclaimer, the term of this patent is extended or adjusted under 35 U.S.C. 154(b) by 0 days.

(21) Appl. No.: 09/309,103

(22) Filed: May 10, 1999

(51) Int. Cl.[7] .................................................. G06K 9/00
(52) U.S. Cl. ......................................... 382/111; 702/34
(58) Field of Search .......................... 382/111; 348/125, 348/128; 356/238, 241, 242, 429, 430; 702/34, 33, 35, 36, 56, 57, 58, 59

(56) References Cited

U.S. PATENT DOCUMENTS

| | | | |
|---|---|---|---|
| 5,125,034 A | * 6/1992 | Hudson et al. | 382/111 |
| 5,276,866 A | 1/1994 | Paolini | 395/600 |
| 5,345,515 A | * 9/1994 | Nishi et al. | 382/111 |
| 5,533,145 A | 7/1996 | Shofner et al. | 382/141 |
| 5,544,062 A | 8/1996 | Johnston, Jr. | 364/468.24 |
| 5,680,473 A | * 10/1997 | Kanzaka et al. | 382/141 |
| 5,725,737 A | * 3/1998 | Pikulik et al. | 162/263 |

* cited by examiner

Primary Examiner—Andrew W. Johns
Assistant Examiner—Seyed Azarian
(74) Attorney, Agent, or Firm—Frommer Lawrence & Haug, LLP; Ronald R. Santucci (57) ABSTRACT

This invention defines a system and method of generating and reporting a fabric analysis to a customer. Information is generated from various tests performed on the fabric. The information gathered from the tests is then digitized in a computer readable format. The digitized information is compiled into an electronic form. The information organized in the electronic form is the fabric analysis report which is delivered to the customer. The amount of time in which this report allows information to be distributed to the customer is greatly reduced and allow providing an additional advantage over the traditional means of reporting.

27 Claims, 7 Drawing Sheets

PAPERMAKING FABRIC ANALYSIS REPORT

FIELD OF THE INVENTION

This invention relates to the field of woven and non-woven papermaking fabric used on papermaking machines in the manufacturing of paper. More particularly, the invention relates to an electronic fabric analysis report and method for communicating the results of test data, physical tests, and analysis performed on a used papermaking fabric from a manufacturer to the customer in an integrated and timely manner. This allows a customer to make higher quality repairs and adjustments to their papermaking machine and to save great expense in reducing downtime and preventing the manufacturing of defective paper.

BACKGROUND OF THE INVENTION

In the papermaking process, huge endless belts referred to as papermaking fabrics are used at different stages of the process to support and transport the paper from a wet pulp to a thin dry sheet. The fabrics range from 25 feet to 300 feet in length and approximately 6 feet to over 33 feet in width. The fabrics are joined or made endless and travel about rollers on the rather large papermaking machine. Depending on how well the machinery is running, and its state of repair, the fabrics become more or less worn. In extreme cases, a problem on the machinery can cause the fabric to wear or be damaged excessively, or even leads to fabric failure. Much expense is caused by these problems.

Disruption of the papermaking process and any resulting down time leads to tremendous loss and expense for the paper manufacturer, especially when a fabric fails and ruins a portion or even the entire paper making run. Additionally, papermaking fabric itself is quite expensive. Ideally, papermaking fabrics are replaced at a point in time before the papermaking fabric fails but after the satisfactory life of the fabric is reached to obtain the maximum use from a papermaking fabric. It becomes very important to obtain as much information concerning the papermaking fabric's wear to know when this time occurs, and maintain machinery in the proper adjustment. Also, it is very important for the paper manufacturer to know why a fabric fails or becomes prematurely worn. The present invention provides much more information in a much more timely fashion over prior manual reporting to help the paper manufacturer overcome these problems.

In the papermaking industry, it has been generally known to perform an analysis of a worn, failed, or damaged papermaking fabric and to report the results of the analysis to the customer in written format. The customer uses this report to make any necessary adjustments or repairs to the papermaking machine. This report can also be used to inform the customer that the fabrics can be left on the machines longer before needing replacement and thus saves the paper manufacturer from unnecessary expense and down time.

Prior to the present invention, results from tests were merely physical compilations of individual results. This manual method lacked the ability to fully explain the results of tests, lacked cohesive data presentation, and made utilization of information difficult for the customer. For example, 35 mm photographs were taken of worn or failed fabrics and simply attached to a written report and not integrated into the report. Results from various physical tests were stapled or otherwise attached to written explanations and photographs, thereby lacking cohesiveness and ready comprehension.

The primary disadvantage of previous manual reporting methods was the required lead time between the customer providing a used or failed fabric for analysis and reporting the results to the customer. In addition, the reports lacked integration so as to be more readily utilized by the customer. Timing can be critical for a customer since a papermaking machine which is continually causing excessively wear, damage, or destroys paper making fabric causes the customer down time, poor production runs and increases expense in replacing failed fabric. Additionally, such problems potentially ruin the paper in production and cause added expense. In the prior manual methods, lead times were necessary since 35 mm photographs and is other data requires development time. The lead time is just increased when the quality of the photographs is not good enough and the photographs must be retaken. Retaking photographs and the associated lead time increases the time and cost to the papermaking customer.

It's generally been known to utilize computerized systems to inspect other objects in non-related fields. For example, U.S. Pat. No. 5,530,652 discloses a device for taking measurements of a human figure and generating a clothing pattern. U.S. Pat. No. 5,345,515 shows a computerized system for inspecting cotton and wool fibers for defects. Another physical analysis system is shown in U.S. Pat. No. 4,276,480 and discloses a method and apparatus for determining properties of a material such as weight or thickness. U.S. Pat. No. 5,146,550 discloses a computerized method of testing textile material and displaying the results in a chart format. These above disclosures are concerned with performing specific physicals tests and are not concerned with the problems solved by an integrated digital readily comprehendible report for a complete fabric analysis.

U.S. Pat. No. 4,546,434 discloses a non-related computerized method for storing and retrieving garment patterns for designing clothing and apparel, an invention unrelated to a digital integrated papermaking fabric analysis report.

While previous methods of reporting have been accepted in the past, the time required to produce these prior reports, the lack of data integrity and integration, and the non-cohesive presentation are disadvantages to which considerable attention is needed to improve product quality and production efficiency for the paper manufacturer.

Accordingly, an object of this invention is to provide an analysis report of papermaking fabric having an integrated, cohesive information presentation format which may be provided to the customer in a timely and efficient manner.

Accordingly, an other important object of this invention is to provide a comprehensive, integrated analysis report of papermaking fabric wherein an analysis based on diverse data inputs may be quickly delivered to a customer in a digital format.

Another object of this invention is to provide an analysis report of papermaking fabric in a format which is readily edited, easily available, and electronically transmitted, thereby reducing the time it takes to report analysis results to the customer.

Another object of this invention is to provide an analysis report of papermaking fabric which allows multiple media to be incorporated into the report to provide more cohesive and comprehensive presentation which gives the customer more complete information to be used when repairing or adjusting a papermaking machine.

Another object of this invention is to provide an analysis report of papermaking fabric which can be readily edited for allowing the salesmen, technicians or other individuals to review and edit the report so that the customer has all the information from these sources integrated into a single location providing more information concerning the papermaking machinery.

Another object of the present invention is to provide an analysis report of papermaking fabric at substantially lower cost.

SUMMARY OF THE INVENTION

The above objectives are accomplished accord to the present invention by producing a digitized analysis report of papermaking fabric comprising digitizing information of the physical characteristics of papermaking fabric derived from the fabric analysis and recording these results in a computer readable medium. The digital format and content of the report allows delivery and presentation to the customer to be done quickly so that the customer can make adjustments and repairs to papermaking machinery, replace a fabric, or know to lengthen the time between fabric replacement; all of which minimizes down time and economic loss.

In essence, the present invention is a method of creating an analysis report of a papermaking fabric used on a papermaking machine. The analysis is reported to a customer so that the customer can quickly determine if or whether abnormal wear has been caused by the papermaking machine as well as to determine if defects exists in the fabric. Also, the customer can determine if the papermaking machinery is operating correctly or if papermaking fabric is being replaced prematurely so that the fabrics have remaining useful life.

The first step is to perform tests to measure physical characteristics of the papermaking fabric selected from at least one of, caliper test, air-permeability test, strength test, weight test, void volume test, hydrolysis test, and water-permeability. The next step is to provide a digital template to receive results from the selected tests. Next, the results from the tests are compiled into a test data set representing the physical characteristics of the papermaking fabric. The data test set is digitized to provide a digital test data set. This digital test data set is placed into a digital template. In addition to the above tests, fabric images are generated of the papermaking fabric and these images are digitizing to provide digital fabric images. These images are placed in the digital template. Fabric video can also be generated to show full motion video of the papermaking fabric analysis or the papermaking fabric. This video is digitized to provide a digital fabric video and is than placed into the digital template. Textual information is also generated from the analysis of the papermaking fabric, digitized and placed into the digital template. The next step is to organize the digital test data set, the digital fabric images, the digital fabric video, and the digital textual information within the digital template so that an easily comprehendible, deliverable, and readable digital fabric analysis report is provided for the customer. This digital report helps the customer better determine wear and damage to the papermaking fabric which may be caused by the papermaking machinery.

Generally, the process for producing the report begins with the customer requesting a fabric analysis. The fabric is than removed from the papermaking machine and physical tests are performed on the papermaking fabric or a sample of the fabric. This analysis is requested for a number of reasons including when the customer's papermaking fabric has been prematurely worn or damaged during the papermaking process. Fabric analysis can also be requested to determine if any defects exist in the papermaking fabric. Also, the customer may desire a report to determine if the papermaking fabric is being replaced too soon. In all cases, it is very desirable to report the analysis back to the customer in a timely fashion to minimize future wear and failure, or to minimize expense to the customer due to premature replacement of fabrics which may have contained more life.

DESCRIPTION OF THE DRAWINGS

The construction and design to carry out the invention will be described, together with other features.

The invention will be more readily understood from a reading of the following specifications and by reference to the accompanying drawings, incorporated by reference, wherein an example of the invention is shown a follows.

DETAILED DESCRIPTION OF THE INVENTION

Figure 1:
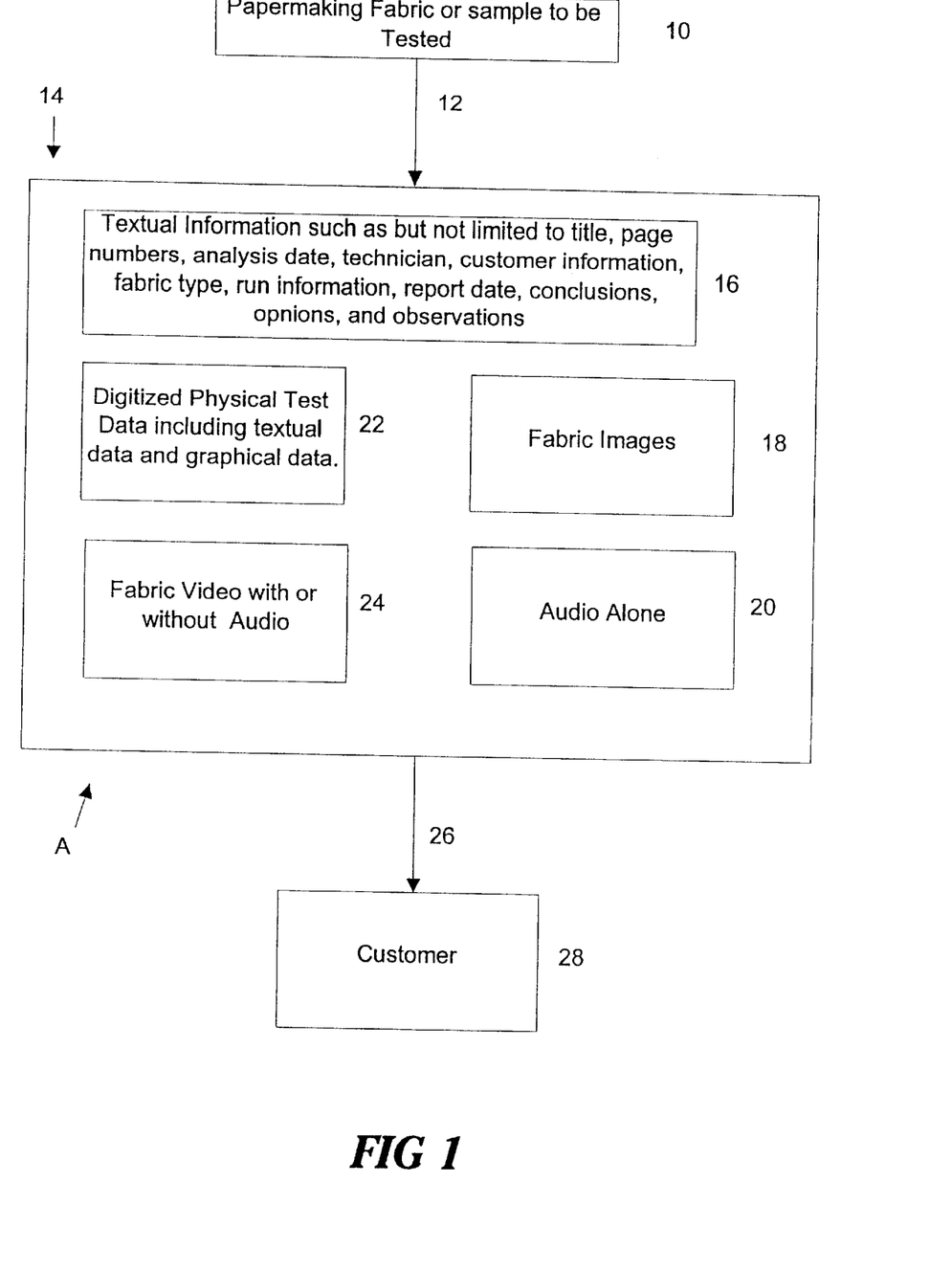
FIG. 1 is a diagram illustrating the digital papermaking fabric report.

Referring in more detail to the drawings, the invention will now be described in more detail. In FIG. 1, the digital test report is generally shown as A. The fabric report is finalized in a digital format which, when displayed or printed, contains information concerning the analysis of papermaking fabric 10 obtained from the customer. In the present invention, the report begins with an electronic template 14 providing a place for containing the results from physical tests and analysis. The digital report contain textual information such as a title, page numbers, the type of fabric analyzed, the customer information, run information on the fabric, the date, recorded observations, opinions, and conclusion concerning the fabric or the fabric analysis as in 16 of FIG. 1. The report may also contain digital physical test information 22, fabric images 18, fabric video information with or without audio 24, or audio information 20. Once compiled and formatted, digital report A is transmitted to customer 28. The means for transportation include delivery of a printed report generated from the digital report, electronically mailing to digital report, and delivering the report on digital medium.

Figure 2:
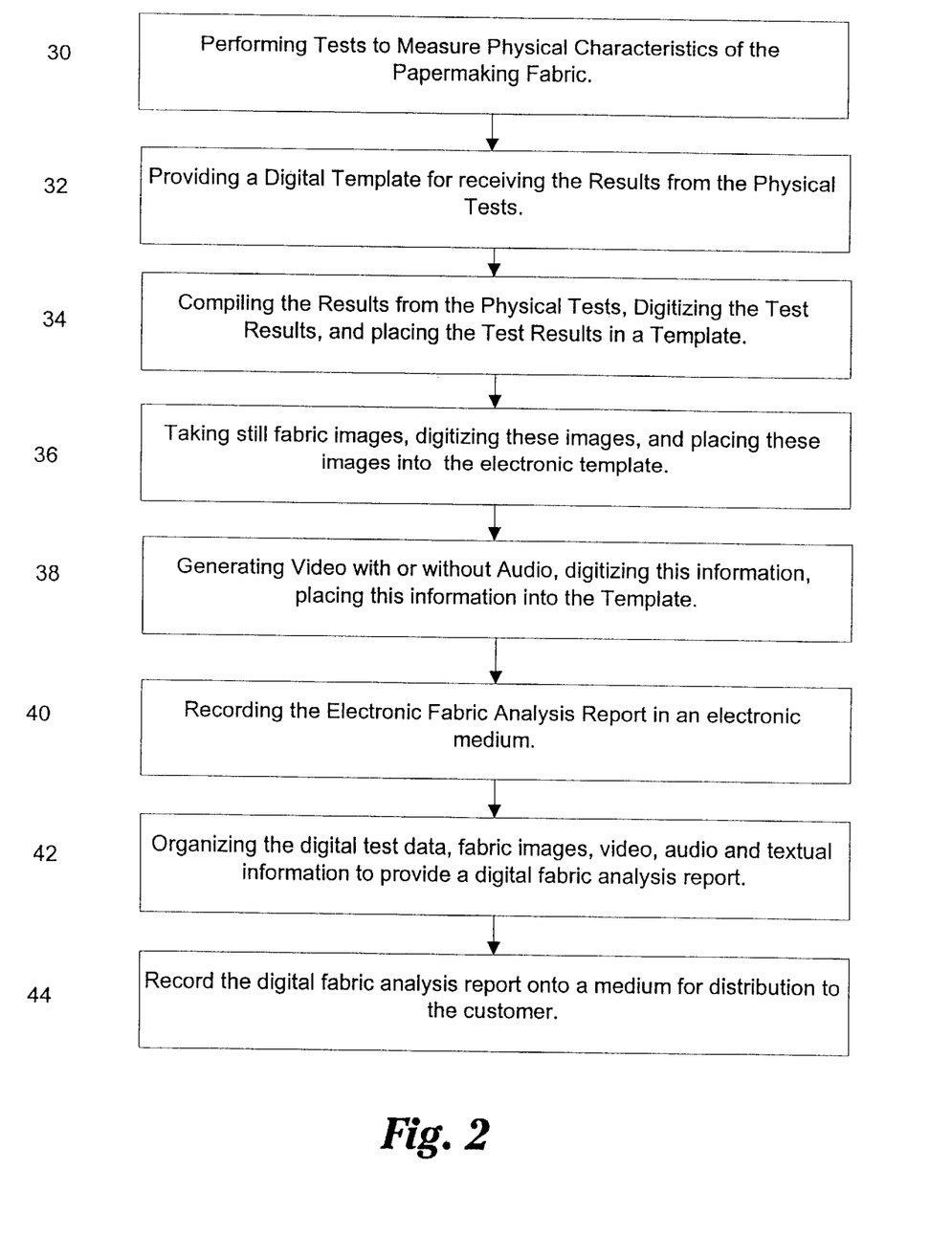
FIG. 2 is a flow diagram illustrating the method of the present invention steps from the fabric analysis to the distribution of the fabric report to the customer.

In FIG. 2, step 30 illustrates the performance of tests to measure the physical characteristics of the papermaking fabric. Next the information is placed in a digital template at 32 to organize the information. Once the physical tests are performed, the information is compiled, digitized and placed into the digital template at step 34. Next still images are taken of the fabric, digitized and placed in the digital template at 36. Video of the papermaking fabric or the fabric technician is generated, with or without audio, and placed into the digital template at 38. The digital report is stored in the computer and recorded in a digital format at 40. The digital report is now organized into the final report at 42 to be distribution to the customer. The digital report can now be recorded on CD-ROM, floppy, zip-disk, or other electronic medium for storage or delivery to the customer at 44.

In the present invention, the analysis report is recorded to a zip-disk using an iomega zip-drive with 100 megabytes capacity. This disk can then be sent to the customer. Another method of transmitting the fabric analysis report to the customer is to transmit the file through electronic mail. While these methods are presently used, those skilled in the art certainly understand that other methods of transmission can be utilized to achieve the same results. This format and method of transmission allow the report to be provided to the customer in a much more timely fashion and greatly enhances the customer's ability to perform repairs and maintenance.

Figure 4:
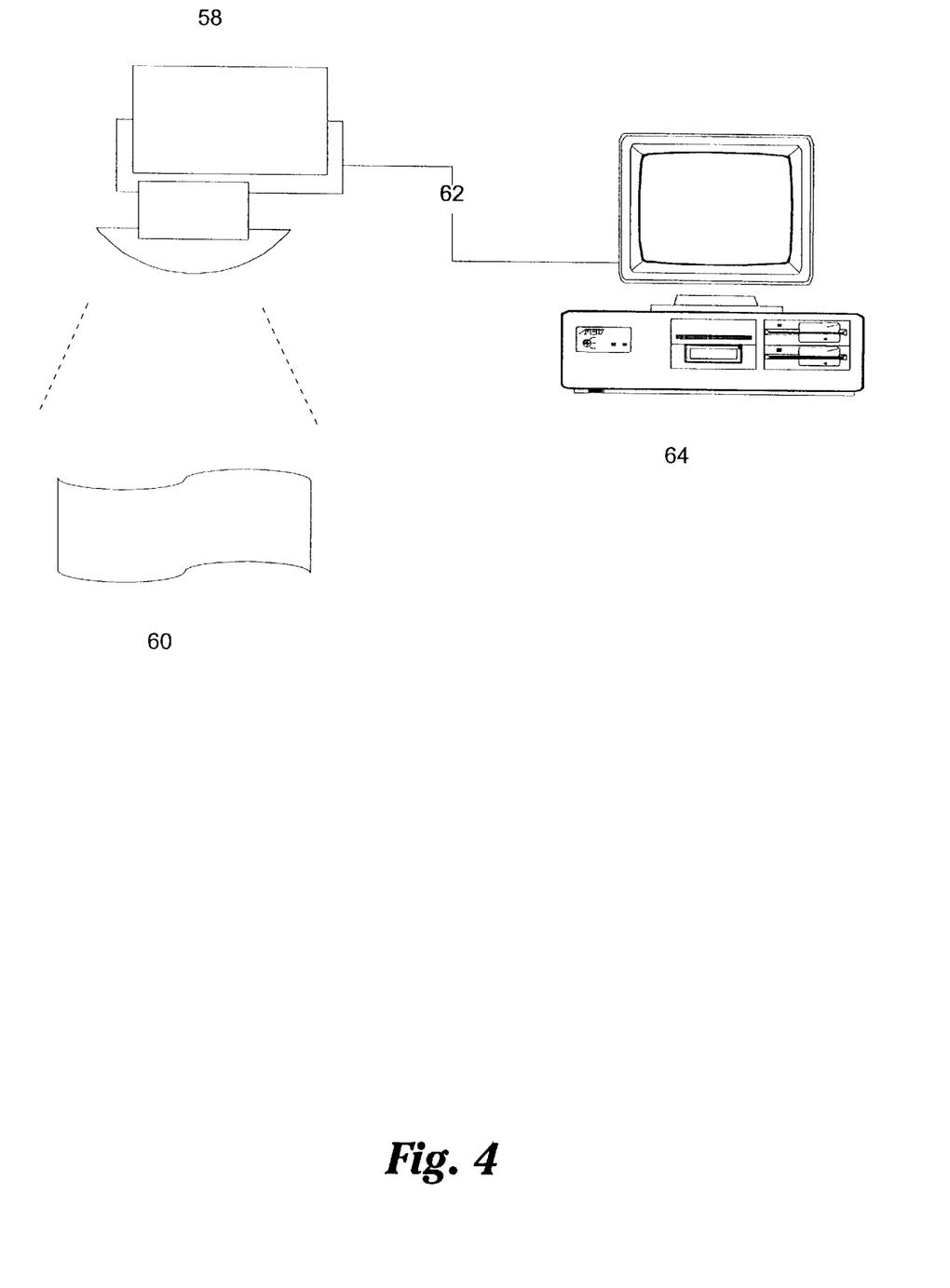
FIG. 4 is an illustration showing the connection of a testing machine or caliper machine to a computer to record test data.

When analyzing the papermaking fabric, several tests maybe performed. One such test is a caliper profiler as illustrated in FIG. 4. In the preferred embodiment, a Emveco Profiler Model # 210A is used to perform the caliper profile.

FIG. 4 illustrate caliper profiler machine 58 connected to computer 64 through RS232 serial cable 62. Fabric 60 is analyzed by caliper profiler 58 and the results are transmitted through cable 62 to computer 64. According to the method, as can best be seen in FIG. 3, the first step is to analyze the fabric with the caliper machine or other physical test at step 46. Next, step 48 shows the results from the testing machinery being recorded. In the case of the caliper machine used in the preferred embodiment, step 50 shows the collected data being transmitted to a computer, such as an IBM ThinkPad Model 760 XD, through a RS232 serial port and stored. Although serial transmission is used in the present invention, those skilled in the art will realize that many other means of data transmission are certainly available. Step 50 also allows for digitization of the collected data. In the present invention, the information is transmitted to the computer through the RS232 port and stored in a text file on the computer. This process of transmitting the information from the caliper machine to the computer results in the information stored in a digital format. Once the caliper information is stored within the computer, the information can be retrieved into a spreadsheet and placed into a graphical format as illustrated by step 54. Most tests, however do not currently allow for direct transmission of data from the test to the computer. Therefore, the information must otherwise be stored, digitized, and recorded in a digital format at 52.

Figure 3:
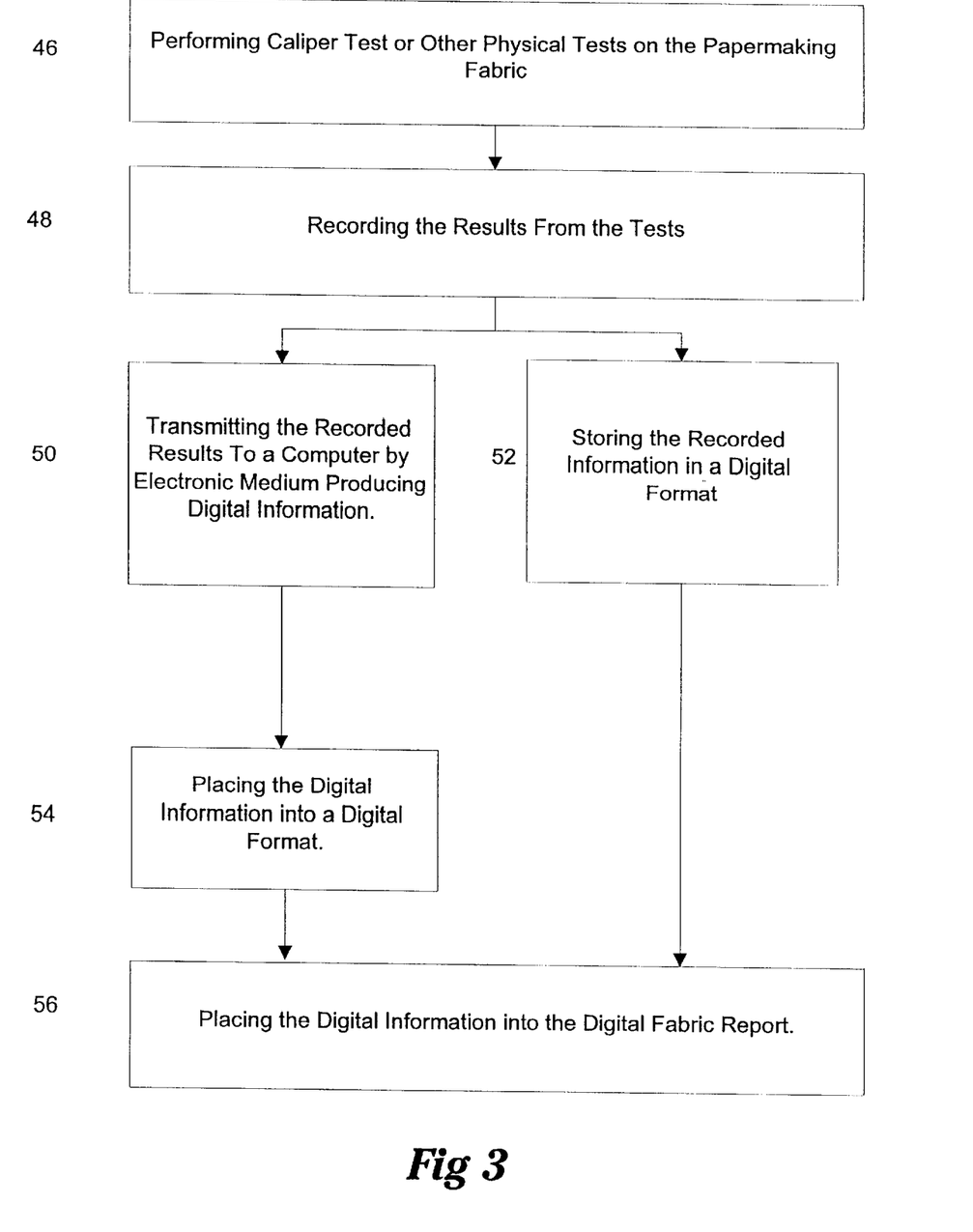
FIG. 3 is a flow diagram illustrating the testing and the test data generation according to the invention wherein analyzing the fabric with test machinery to including the recorded information from the test machinery into the fabric report is exemplary.

As this point, the graphical information can be organized and placed into the electronic template as shown in step 56. Such graphical information is a much more informative format than merely a text representation of the information. Following is an example of graphical information of caliper and air-permeability test results.

Figure 5:
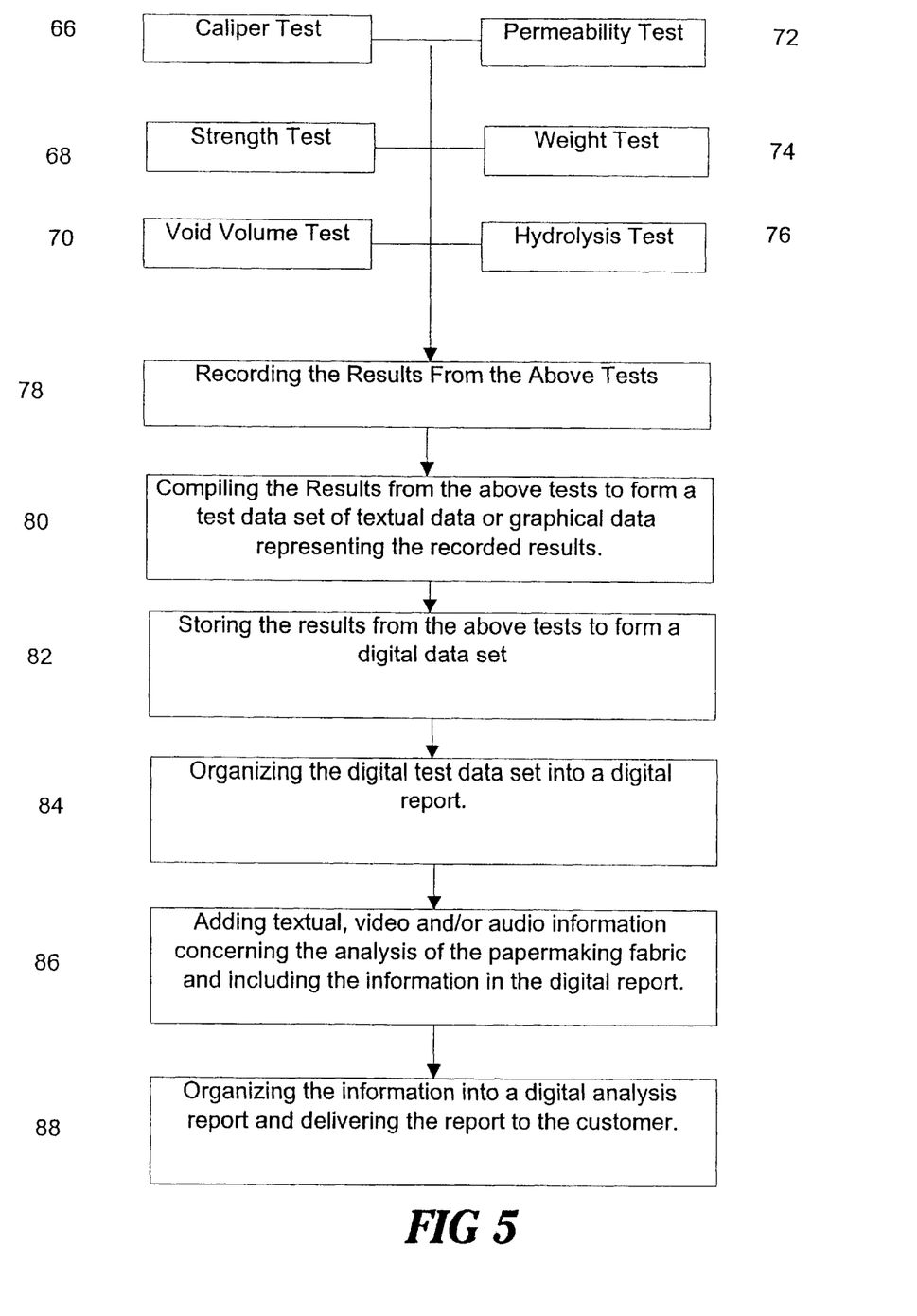
FIG. 5 is a flow diagram illustrating the steps from performing physical tests to compiling the data for insertion into the fabric report.

The other physical tests performed during the analysis of papermaking fabric are shown in FIG. 5 and included permeability test 72, strength test 68, weight test 74, void volume teat 70 and hydrolysis test 76 as well as caliper test 66. Although the fabric analysis machines used for these tests do not necessarily have to transmit information directly to the computer the next step is still to record the results form these tests at 78. This recorded fabric information is compiled and digitized into digital information at 80. The compiled fabric information, textual or graphical, is stored to form a digital data set containing the physical characteristics of the papermaking fabric at 82. This digital data set is then placed into the digital report and organized into a fabric analysis report at 84. It should be noted digitizing the fabric test data can be performed in various ways based upon the information to be digitized. For example, traditional 35 mm photographs can be scanned into the computer, text information can be scanned or typed into the computer, and graphical information can be typed in as raw data with the computer producing the graphical representation. These various formats integrated into one report better inform the customer in a more timely fashion and to what steps should be taken with respect to the papermaking fabric and papermaking machinery. Any video or audio information is included in a digital format in the digital report at 86. The complete results from the physical tests, video and audio as well as textual information later added is organized into a digital report ready for delivery to the customer at 88.

Figure 6:
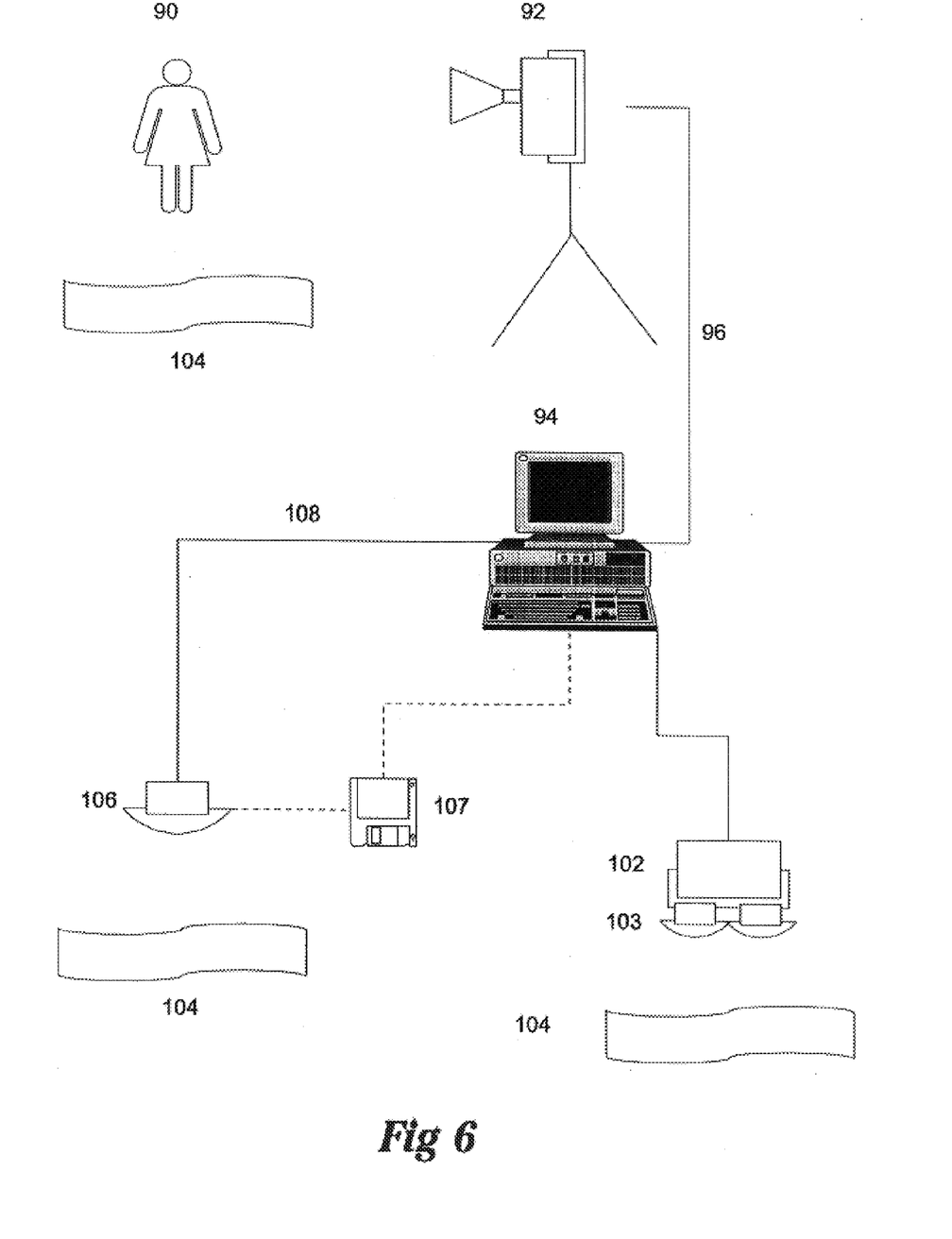
FIG. 6 is an illustration of the connection of the digital camera, microscope and computer.

Visual and audio information concerning the fabric analysis can be placed in the fabric report. FIG. 6 illustrates how to place full motion video into the fabric analysis report. In the preferred embodiment, video camera 92 is connected to computer 94 through cable 96. Technician 90 is videoed along with papermaking fabric 104 and the recording is stored on the computer. In the preferred embodiment, the video camera is manufactured by Sony and has model number VK C370W DSP. The IBM ThinkPad Model 760 XD is a laptop computer with which allows for the video camera to be connected directly to the computer. The video and the audio information is stored in a Audio Video Interleave (AVI) format utilizing Asymetrix DVP Capture software which digitizes the information from the video equipment and stores the information on the computer. Once video is taken, it is combined with other tests into the analysis report, as shown in steps 30 through 44 of FIG. 2, to provide the analysis report. This ability allows the technician or other individual to provide lecture like voice instruction along with video concerning the analysis of the papermaking fabric as if the customer were standing with the technician.

FIG. 6 also illustrates the connection between a digital camera and the computer. Digital camera 106 is can be connected to the computer in any manner which allows transmission of the digital image to the computer. One such connection is through serial line 108. In the preferred embodiment, a Sony MVC-FD71 Digital still camera 102 is used to photograph aspects of the fabric analysis. The digital camera converts still images into digital image data so that the images can be stored in a format such as Joint Photographic Experts Group (JPEG or JPG). One skilled in the art will realize that any image format readable by the computer can be used and JPEG is not necessary for this invention, For example, in the preferred embodiment, the digital camera can store a digital image on floppy disk 107. This floppy disk can be used to transfer the digital image to the computer where it can be placed into the digital report. In addition to floppy disk 107, a capture card can be used transfer images from the digital camera to the computer for insertion into the digital report.

The digital camera can also be connected to a microscope 103 to provide magnified images of papermaking fabric 104. In the preferred embodiment, an Olympus SZH microscope has a Hitachi VK-C370W DSP video camera attached to record these magnified images. Both the digital images and the magnified digital images better illustrate the papermaking fabric, allowing visual comparison of a fabric and provide illustration for the analysis and opinion all contained in one digital format. This allows the customer to have significantly more information concerning the papermaking fabric and the papermaking industry. Such an image is shown in FIGS. 7 and 8 showing a comparison of the top of a fabric shown in FIG. 7 and the bottom of a fabric shown in FIG. 8.

Figure 7:
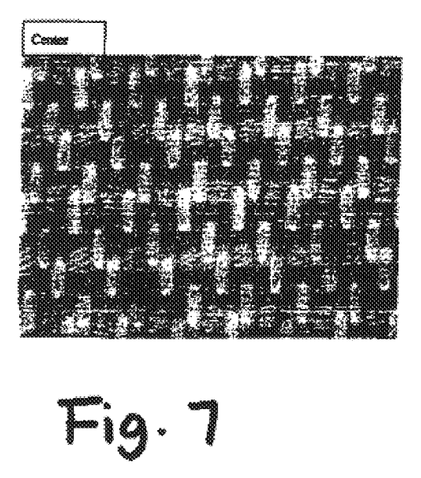
FIG. 7 is a perspective view of the top of a fabric.
Figure 8:
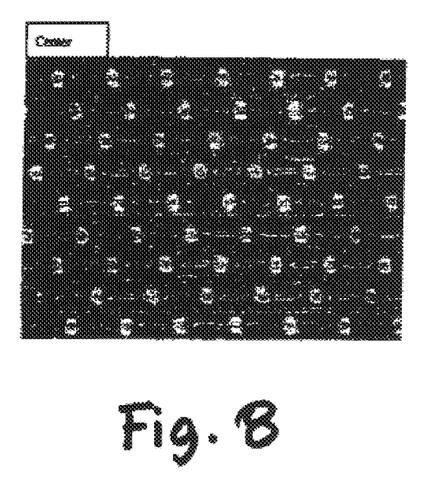
FIG. 8 is a perspective view of the bottom of a fabric.

The same information can be provided showing a new fabric in FIG. 7 and a used or worn fabric shown in FIG. 8. Such a comparison within a single electronic format allows the customer to have considerable more information to help analyze the performance of the papermaking machine.

In addition to the above information, audio information alone can be digitally included in the fabric analysis report. In the preferred embodiment, the IBM ThinkPad Model 760 XD contains a built-in microphone which records audio and can store the digitized information on the computer. Microsoft sound recorder software is used to digitize the audio information and store it electronically on the computer. The sound recorder software is packaged with Microsoft Windows products. Once the audio information is digitized and stored on the computer, the audio information can be placed in the fabric report.

Once information, whether from the test results, the video camera, the digital camera or the audio information, is collected, the information must be integrated into a analysis report. This step is shown in FIG. 2, step 38. In the preferred embodiment, the format of the consolidated report is initially in a word processor such as Microsoft Word. From this stage, the report can be electronically recorded in several formats. In the present invention, the final analysis report of the papermaking fabric is in an Adobe Acrobat format which is a computer readable format generally designated with the .pdf file extension. However, those skilled in the art will know that other formats can also be utilized.

Once completed, the analysis report can be transferred to a digital medium such as a writeable CD-ROM manufactured by Hewitt Packard and sold as the CD Writer Plus Model # 7110 which is a readable-writeable CD-ROM. Additionally, one skilled in the art would understand that the Zip-Drive technology would be just as effective. This electronic medium is then distributed to the customer either by sending a computer disk containing the file of the fabric analysis report of by electronically mailing the file to the customer.

Generally, the test results measuring physical characteristics are recorded either manually by the operator or transmitted directly to a computer. Such physical test data may include, fabric caliper readings, air-permeability readings, hydrolysis readings, water-permeability readings, void volume measurements, and weight. This information allows the customer to determine the causes of wear or failure as well as any potential life left in a fabric.

Once collected, the data from these tests is digitized onto a computer readable format and formatted into a digitized report. In the present invention, an electronic template is used to assist in the organization of the various data sets into the report.

Before incorporation into the electronic template, the test data exists in such formats as spreadsheets, graphs, and text. For example, some caliper machines can transmit information directly to a computer. The transmitted information can then be retrieved directly into a spreadsheet. The spreadsheet information is then formatted into graphs. The graphs are then incorporated into the fabric analysis report thereby providing a graphical representation of the caliper profile. The incorporation provides a report with a single presentation containing information from multiple sources and allows the customer to more readily understand the analysis of the papermaking fabric. Of course a manual caliper analysis can be performed and the information can be entered by hand into the spreadsheet and the same results are achieved.

Along with physical tests, a visual inspection of the papermaking fabric as well as a verbal description and the opinions of the technician concerning the papermaking fabric are digitized and incorporated into the fabric analysis report. Therefore the fabric analysis report can contain sound recording of the technician's visual inspections and explanation of the test results so that the customer has more complete information to repair or replace the papermaking fabric. The addition of motion video allows instruction to be given to the customer in a lecture format to explaining the test data and allows a technician to point to and show the customer the relevant parts of the papermaking fabric. The customer can view this recorded presentation allowing the customer to receive the full benefit of the technician's analysis without having to schedule an appointment and physically visit the technician's location. Motion video provides an explanation concerning the fabric analysis as if the customer were present with the technician.

Images of the fabric, including magnifications, help illustrate the finding of the analysis. In the present invention, images are produced by taking a picture with a digital camera and transmitting the image to a computer. Magnification images are produced by placing a digital camera on a microscope, taking the picture through the microscope, transmitting the image to a computer, and incorporating the image into the fabric report. Digitization of analog images can be converted to a digital signal through analog digital converters connected between the camera and the computer. On such analog to digital product is marketed under the trademark SNAPPY®. When images of a new and used fabric as included in the analysis report, the customer can see a comparison between the used or failed fabric and a new undamaged fabric to compare the differing physical characteristic.

The utilizing of digital images overcomes traditional problems with 35 mm photography. Those skilled in the art know that the margin for error in photographic development is greater and the lead time for obtaining the final print or slide is longer. Utilizing digital images in the electronic fabric analysis report reduces both the time and the expense necessary for photo images in both producing and integrating images into a report. Digital images can be immediately reviewed for such problems as too little light, out of focus, or poor contrast. These errors can be instantly corrected and therefore the images are immediately available for placement into the fabric report.

Additionally, the present invention allows for viewing images on a computer screen therefore providing brighter and better clarity since the image is projected on a screen and not on photographic paper.

The digital format of the information also allows the report to be easily viewed and edited. Therefore the papermaking fabric manufacturer can more easily tailor the analysis report to the specific needs of the customer by have various individuals review and edit the analysis report. The traditional, physical report made review and edits of the manufacturing representative, the technician and the salesman difficult and lengthened the time between performing the tests and reporting the results. With the present invention, the technician can provide the report to the manufacturer and salesman for immediate review and edits. This ability allows the customer to benefit from the analysis and opinions of the fabric manufacturer, technician, and salesman all contained in one easy to understand, integrated single report, delivered within a timely fashion. Prior manual reporting simply does not allow the above extensive reviews and edits of the report by the various individuals.

The digital format also allows for the transmission of the analysis report to various individuals through communication means such as Internet e-mail, interoffice e-mail, CD-ROMs, zip-drives, floppy disks, or other digital medium. The ability to electronically store and transmit the analysis report allows the papermaking customer to receive the information in a much more timely fashion. This allows the customer to more quickly remedy any problems identified in the analysis report.

The digital format also facilitates storage of analysis reports. The customer can quickly retrieve past reports to examine the history of analysis for specific papermaking machines. For example, the customer can review the caliper profile for the last several used or failed fabrics and potentially spot a trend occurring within the papermaking machine. Such information greatly increases the ability of the papermaking customer to anticipate problems and perform preventive action.

While the preferred embodiment of the invention has been described using specific terms, such description is for illustrative purposes only, and it is to be understood that changes and variations may be made without departing from the spirit or scope of the following claims.

What is claimed is:

1. A method of generating a digital report of an analysis of a papermaking fabric used on a papermaking machine wherein the papermaking fabric travels on the papermaking machine in the form of an endless belt, and the analysis is reported to a customer so that the customer may quickly determine whether abnormal wear or damage to the fabric has been caused by papermaking machine, or whether defects exists in the fabric, or improper machine operation has occurred, wherein the method comprises:

performing a plurality of tests on a papermaking fabric while said fabric is off of said papermaking machine to provide test results of certain physical characteristics of said papermaking fabric;

recording said test results of said physical characteristics of said papermaking fabric;

performing a caliper test in said plurality of tests, and compiling a caliper data set representing the caliper information of the fabric, said caliper data set being included in said test results;

performing an air-permeability test in said plurality of tests representing the air-permeability of said papermaking fabric, and compiling said air-permeability data set which is included in said test results;

compiling said test results into a test data set which represents said physical characteristics of said papermaking fabric;

storing said test data set in a digital format on a computer readable medium to provide a digital test data set representing said physical characteristics of said papermaking fabric;

organizing said digital test data set into a digital report of said papermaking fabric analysis;

including textual information concerning said papermaking fabric analysis and included said textual information in said digital report; and, delivering said digital report to said customer so that said customer is provided with a timely and comprehensive digital report which may be displayed by the customer on a computer.

2. The method of claim 1 including recording still fabric images of a select portion of said papermaking fabric, digitizing said fabric images into a digital fabric image data set, and compiling said digitized fabric images into said digital report.

3. The method of claim 2 including recording fabric video of said papermaking fabric analysis, digitizing said fabric video into an electronic format, and compiling said digitized fabric video into said digital report.

4. The method of claim 3 wherein performing said physical tests on a papermaking fabric further comprises performing a strength test and compiling a strength data set representing the strength characteristics of said papermaking fabric, storing said strength data in a digital strength data set, and including said digital strength data in said digital test data set.

5. The method of claim 4 wherein performing said physical tests on a papermaking fabric further includes weighing said fabric, compiling weight data into a weight data set representing the weight information os said papermaking fabric, recording said weight data set in a digital weight data set, and including said digital weight data set into said digital report.

6. The method of claim 5 wherein performing said physical tests on a papermaking fabric further comprises performing a void volume test, recording void volume data into a void volume data set representing the void volume measurement of said papermaking fabric, compiling said void volume data set into a digital void volume data set, and including said digital void volume data set into said digital report.

7. The method of claim 6 wherein performing said physical tests on a papermaking fabric further comprising the step of performing an water-permeability test, storing water-permeability data into a digital water-permeability data set representing the water-permeability information of said papermaking fabric, and including said digital water-permeability data set in said digitized report.

8. The method of claim 3 further including formatting said digital test data set, said digital fabric images and said digital fabric video in a predetermined digital report template.

9. The method of claim 1 further including compiling said caliper data set into a graph format providing a graphical representation of said caliper information, storing said graphical representation of said caliper information in a digital format providing a digital caliper graph, including said digital caliper graph in said digital report.

10. The method of claim 9 further including compiling said air-permeability data set into a graph format providing a graphical representation of said air-permeability information, storing said graphical representation of said air-permeability information in a digital format providing a digital air-permeability graph, including said digital air-permeability graph in said digital report.

11. A method of creating an analysis report of a papermaking fabric used on a papermaking machine wherein the papermaking fabric travels on the papermaking machine in the form of an endless belt and the analysis is reported to a customer so the customer can quickly determine if wear or whether abnormal wear has been caused by the papermaking machine, or whether defects exists in the fabric, if improper machine operation has occurred, or if fabric replacement is occurring when the fabrics have remaining useful life, wherein the method comprises:

performing tests to measure physical characteristics of said papermaking fabric selected from at least one of, caliper test, air-permeability test, strength test, weight test, void volume test, hydrolysis test, and water-permeability;

providing a digital template for received results from said selected tests;

compiling said test results from said selected tests into a test data set representing the physical characteristics of said papermaking fabric, digitizing said test data set into a digital format providing a digital test data set, placing said digital test data set into a digital template;

generating still fabric images of said papermaking fabric, digitizing said fabric images to provide digital fabric images, and placing said digital fabric images into said digital template;

generating fabric video of a papermaking fabric analysis showing full motion video of said papermaking fabric analysis, digitizing said fabric video to provide a digital fabric video, placing said digital fabric video into said digital template;

generating textual information from said analysis of said papermaking fabric, digitizing said textual information, placing said digital textual information into said digital template; and, organizing said digital test data set, said digital fabric images, digital fabric video, and said digital textual information within said digital template so that an easily comprehendible, deliverable, and readable digital fabric analysis report is provided for the customer so that the customer may better determine wear and damage to said papermaking fabric due to said papermaking machinery.

12. The method of claim 11 further comprising the steps of generating audio fabric information from said analysis of said papermaking fabric, digitizing said audio fabric information providing digital fabric audio, and placing said digital fabric audio into said digital template.

13. The method of claim 12 wherein said digital fabric audio is synchronized with said fabric video providing full motion fabric video with fabric audio.

14. The method of claim 13 further comprising the step of recording said digital fabric analysis report on a transportable digital medium for easy distribution to said customer.

15. The method of claim 14 further comprising the step of transmitted said digital fabric analysis report to said customer through an electronic medium.

16. A digital fabric analysis report of a papermaking fabric used on a papermaking machine wherein the report contains the results from one or more physical tests showing the papermaking fabrics physical characteristics as well as the analysis and results derived from said physical tests allowing a paper manufacturing customer to determine abnormal wear, damage, or abnormal machine operation as well as premature replacement of said papermaking fabric, wherein the report comprises:

digital fabric data set of said test results of said physical tests representing said physical characteristics of said papermaking fabric;

digital caliper information included in said digital fabric data set derived from a caliper test performed on said papermaking fabric and representing caliper characteristics of said papermaking fabric;

digitized fabric permeability information from an fabric permeability test performed on said papermaking fabric, said fabric permeability information representing the permeability characteristics of said papermaking fabric and included within said digital fabric data set;

digital fabric images of said papermaking fabric showing the visual characteristics of said papermaking fabric;

digital textual information containing opinions from said analysis if said papermaking fabric; and, said digital fabric data set, said digital fabric images, and said fabric digital textual information is organized to provide an easily comprehendible, transportable, and readable digital fabric analysis report for the customer so that the customer may better determine wear and damage to said papermaking fabric due to said papermaking machine for carrying out machinery adjustments.

17. The report of claim 16 further including a digital template for containing said digital fabric data set and said digital textual information so that a comprehensive report can be quickly generated providing the customer with a fabric analysis of said papermaking fabric.

18. The report of claim 17 further comprising graphical information derived from said caliper data set and showing said caliper characteristics represented in a graphical format to better understand the results from said caliper test.

19. The report of claim 16 further comprising graphical information derived from said permeability data set and showing said permeability characteristics represented in a graphical format to better understand said air-permeability information.

20. The report of claim 19 wherein said digital fabric permeability information includes results from an air-permeability test providing an air-permeability data set representing the air-permeability characteristics of said papermaking fabric, said air-permeability data set is included within said digital fabric data set.

21. The report of claim 20 wherein said digital fabric permeability information includes results from an air-permeability test providing an water-permeability data set representing the water-permeability characteristics of said papermaking fabric, said water-permeability data set is included within said digital fabric data set.

22. The report of claim 21 further including digital video of said papermaking fabric and of a technician performing said analysis of said papermaking fabric allowing the customer to see full motion video of comments made by said technician concerning said papermaking fabric as if said customer was physically present with said technician.

23. The report of claim 22 further including digital audio of said analysis of said papermaking fabric allowing said customer to hear opinions concerning said papermaking fabric.

24. The report of claim 23 wherein said audio is synchronize with said video allowing said customer to see and hear the results from said fabric analysis.

25. The report of claim 16 wherein:

a used fabric data set representing an analysis on a used fabric showing the physical characteristics of said used papermaking fabric;

a new fabric data set representing an analysis on a new fabric showing the physical characteristics of said new papermaking fabric; and, said used fabric data set and new fabric data set are included in said electronic template allowing the customer to compare the physical characteristics of said new papermaking fabric with said used papermaking fabric.

26. The report of claim 16 wherein said digitized data set are organized in a single digital format providing an easily transportable, computer readable analysis report of said papermaking fabric.

27. The report of claim 21 wherein said digital data set is transmitted to said customer in by electronic medium.

* * * * *